US00PP37375P3

(12) United States Plant Patent
Giménez et al.

(10) Patent No.: US PP37,375 P3
(45) Date of Patent: Apr. 21, 2026

(54) STRAWBERRY PLANT NAMED 'LBR 96 1'

(50) Latin Name: ***Fragaria* X *ananassa* Duch.**
Varietal Denomination: LBR 96 1

(71) Applicant: INSTITUTO NACIONAL DE INVESTIGACION AGROPECUARIA, Montevideo (UY)

(72) Inventors: Gustavo Giménez, Canelones (UY); Alberto Lenzi, Canelones (UY); Facundo Ibañez, Canelones (UY); Alicia Castillo, Canelones (UY)

(73) Assignee: INSTITUTO NACIONAL DE INVESTIGACION AGROPECUARIA, Montevideo (UY)

( * ) Notice: Subject to any disclaimer, the term of this patent is extended or adjusted under 35 U.S.C. 154(b) by 0 days.

(21) Appl. No.: 17/803,542

(22) Filed: Aug. 17, 2022

(65) Prior Publication Data

US 2023/0389456 P1 Nov. 30, 2023

Related U.S. Application Data

(60) Provisional application No. 63/259,998, filed on Aug. 27, 2021.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

PUBLICATIONS

CPVO Application Consultation Version 4.12.6 for 'LBR 96 1'; Nov. 2, 2023; 3 pages.*
Pluto Upovrom Plant Variety Database Citation for 'LBR 96.1' as per UY_2020186_NLI; Jan. 20, 2021; 1 page.*
Pluto Upovrom Plant Variety Database Citation for 'LBR 96.1' as per UY_2020186_PBR; Jan. 20, 2021; 1 page.*
http://www.inia.uy/Documentos/P%C3% BAblicos/Llamados%20licenciamiento%20de%20cultivares/BASE%20LLAMADO%20FINAL%20LBR%2096.1%2029%20oct.pdf; Nov. 24, 2020; 20 pages.*
Gimenez et al.; INIA LBR 96.1: sabor, aroma y sanidad en un nuevo cultivar de frutilla de dia neutro; Sep. 2020; pp. 77-81.*

* cited by examiner

*Primary Examiner* — Kent L Bell
(74) *Attorney, Agent, or Firm* — Svendsen Legal, LLC

(57) ABSTRACT

A new day neutral strawberry plant named 'LBR 96 1' is disclosed, with remarkable fruit and flavor characteristics and high levels of resistance to pest and discases.

4 Drawing Sheets

Genus and species: *Fragaria* X *ananassa* Duch.
Variety denomination: 'LBR 96 1'.

STATEMENT REGARDING FEDERALLY SPONSORED RESEARCH OR DEVELOPMENT

None

BACKGROUND OF THE INVENTION

'LBR 96 1' was obtained from a breeding program located in Canelones, Uruguay. It originated from the cross between two advanced clones that was carried out in 2012 in Canelones, Uruguay. It was selected from a field of individuals in 2014 and later evaluated in preliminary and advanced agronomic trials against reference varieties, always under conditions representative of the production technology of the Salto area, Uruguay.

'LBR 96 1' was simultaneously characterized by its sanitary behavior against the natural infection of root/crown, foliar, and fruit pathogens (2014-2019). During 2018 and 2019, it was evaluated at the productive level in the producer's farms. During the last three years physical, chemical, and quality of fruit has been characterized. In 2020, the cultivar was registered, protected, and licensed.

Compared to its maternal parent 'LBK 36.1A' (commercially known as INIA Mayte™—unpatented), 'LBR 96 1' is more tolerant to soil, foliar and fruit diseases with fruit quality and agronomic behavior. According to the information available, 'LBR 96 1' would be recommended for the south production region of Uruguay.

The new cultivar 'LBR 96 1' exhibited early productivity (harvests July-September) and total production (harvest autumn, spring, and summer); and showed a high fruit quality, especially flavor; and health, due to its lower incidence of botrytis and powdery mildew in leaf and fruit.

Comparison is made between new cultivar 'LBR 96 1' and commercial variety 'San Andreas' (U.S. Plant Pat. No. 19,975). 'LBR 96 1' has had higher early yields between June and October than that of 'San Andreas'. 'LBR 96 1' has also maintained a higher total yield throughout growing season of Spring until end of January than that of 'San Andreas'. During trials 'LBR 96 1' maintained an average Soluble Solids of 0.6 (g/100 mL) acidity, 0.8 (N) firmness, and 7.6 brix which provides a balanced fruit. In comparison during trials, 'San Andreas' maintained an average soluble solids of 0.7 (g/100 mL) acidity, 0.9 (N) firmness, and 7.9 brix. In addition, 'San Andreas' is very susceptible to anthracnose, botrytis, leaf spots, bacteriosis and soil diseases whereas 'LBR 96 1' has proven resistance to anthracnose, leaf spots, bacteriosis, powdery mildew, and botrytis.

Throughout several generations of asexual propagation, 'LBR 96 1' has been observed to be stable and retain its distinctive characteristics, and reproduce and remain true to type in successive generations of asexual production.

BRIEF DESCRIPTION OF THE PHOTOGRAPHS

Figure 1:
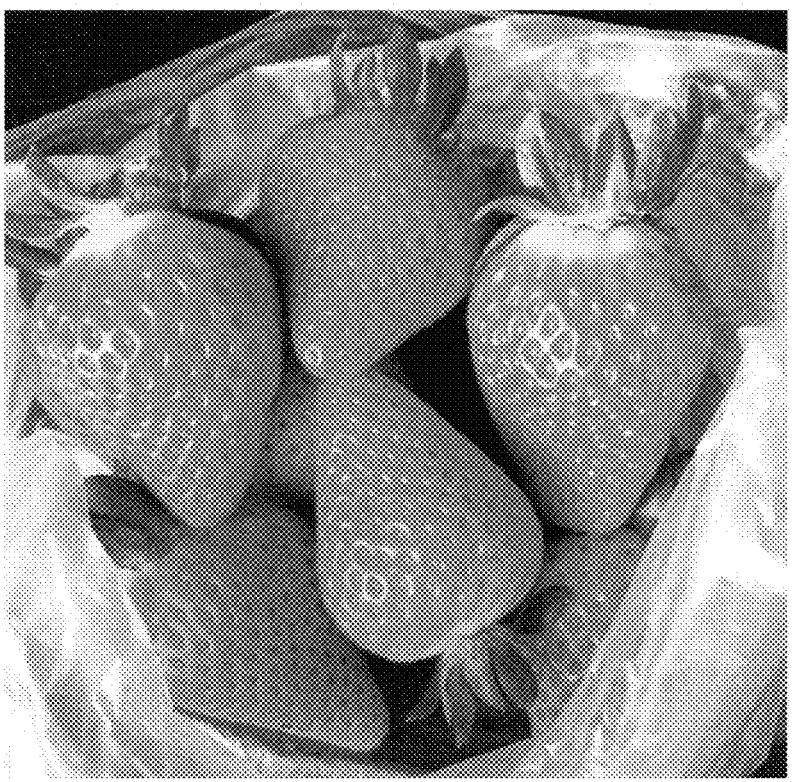
FIG. 1 illustrates the fruit of 'LBR 96 1' harvested July 2021 from a 5-month-old plant.
Figure 2:
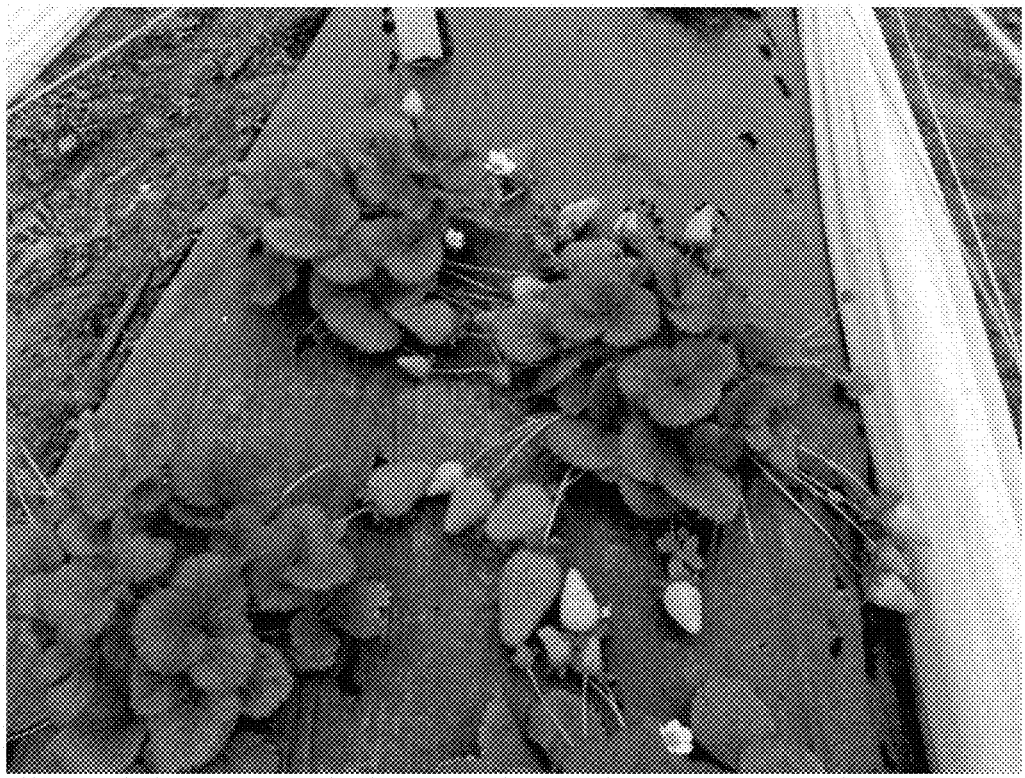
FIG. 2 illustrates plants of 'LBR 96 1' at 5 months of age cultivated with black plastic mulch and drip irrigation.
Figure 3:
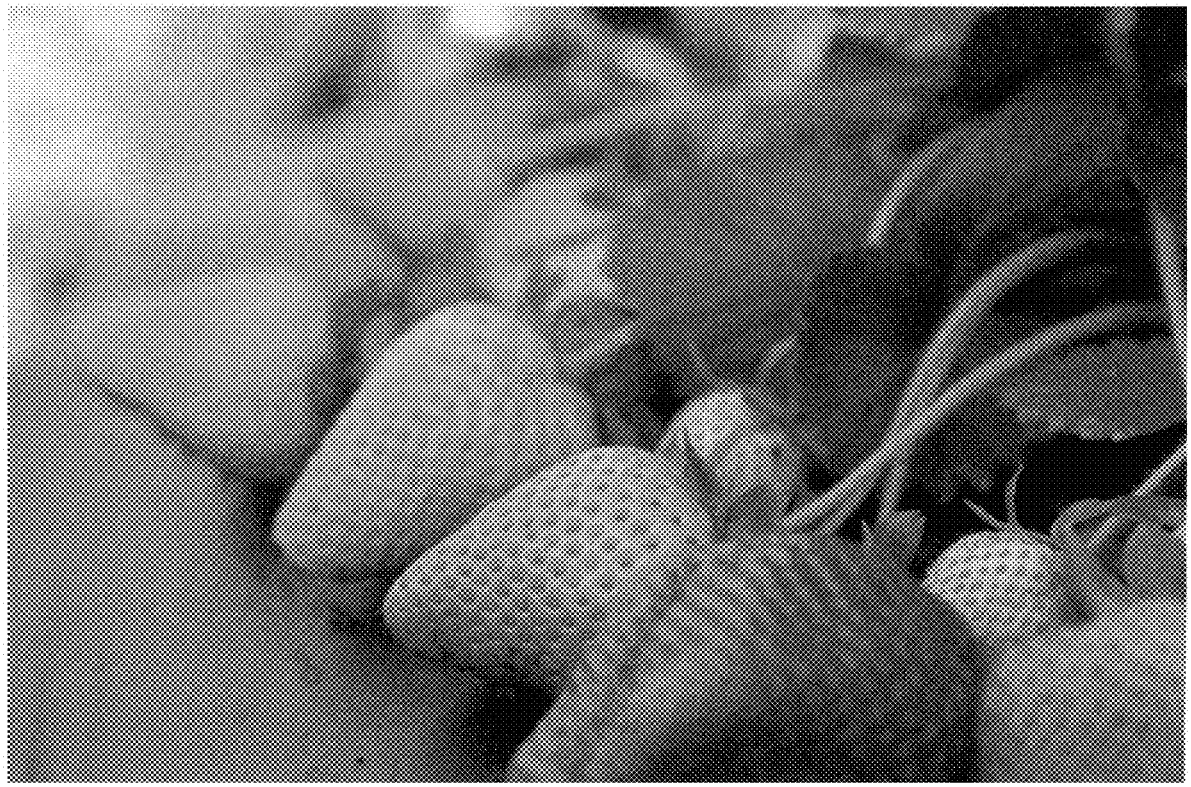
FIG. 3 illustrates plants of 'LBR 96 1' at 5 months of age with ripe fruit just before harvest.
Figure 4:
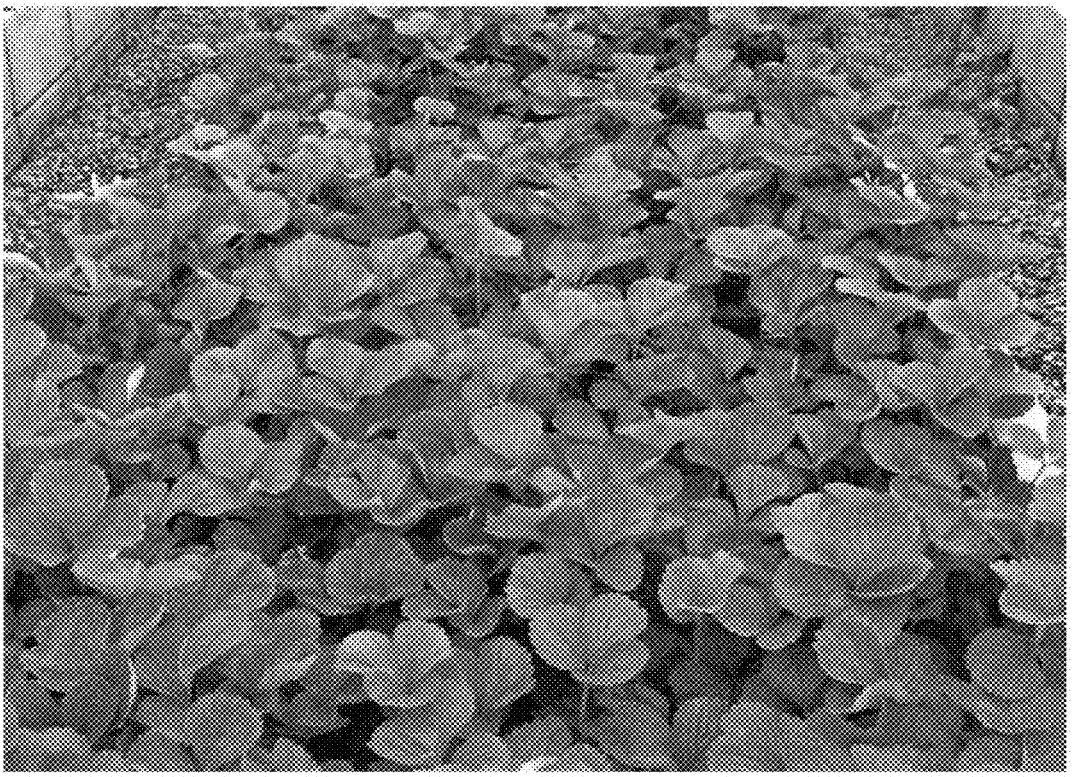
FIG. 4 illustrates production of stolons within a greenhouse with drip irrigation.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is that of a plant age of approximately 3.5 months and is based on observations made during the 2021 growing seasons in Las Brujas, Canelones, Uruguay. It should be understood that the characteristics described will vary somewhat depending upon cultural practices and climatic conditions and can vary with location and season. Measurements are the average for the plants of the new cultivar and may vary according to the stage of development. Color terminology follows The Royal Horticultural Society Colour Chart, London (R.H.S.) (Sixth Revised Edition, 2015).

General description:

*Ploidy*.—Octoploid.

*Blooming period*.—March through April of the following year in the Southern Hemisphere.

*Plant type*.—Day Neutral.

*Plant habit*.—Erect.

*Plant height*.—16 to 22 cm.

*Plant spread*.—26 to 29 cm.

*Plant hardiness*.—4 degrees C. (USDA plant hardiness scale Zone 10b) to 42 degrees C.

*Root description*.—White Group 155 A (Pale Yellow Green). Fibrous roots. Time to initiate roots is on average 5 to 7 days. Time to obtain a fully rooted plant is on average 1 to 2 months.

*Propagation*.—By runners tips, cutting and direct rooting in trays.

*Growth rate*.—Medium vigor.

Stolon description:

*Number of stolons*.—Typically 20 to 30 depending on environmental conditions, 25 observed on average.

*Stolon length*.—35 to 40 cm observed on average.

*Stolon diameter*.—3 mm observed on average.

*Stolon texture*.—Soft.

*Stolon anthocyanin*.—Weak or not present.

*Stolon color*.—Variable; Green Group 140 D (Light Yellowish Green), or with Red-Purple Group 69 B (Very Pale Purple) or Red-Purple Group 65 D (Pale Purplish Pink) when weak anthocyanin coloration observed.

Foliage description:

*Leaf division*.—Typically three leaflets per leaf.

*Leaf size in length*.—8 to 9 cm.

*Leaf size in width*.—14 to 16 cm.

*Leaflet blistering*.—Medium.

*Leaflet glossiness*.—Medium.

*Leaflet variegation*.—Absent.

*Leaflet arrangement*.—Spiral arrangement.

*Leaflet shape in cross section*.—Acute.

*Leaflet length in relation to width*.—Shorter.

*Leaflet length*.—6.0 to 7.5 cm.

*Leaflet width*.—7.5 to 8.5 cm.

*Leaflet margins*.—Serrate to Crenate.

*Leaflet base*.—Obtuse.

*Leaflet apex*.—Rounded.

*Leaflet texture* (*both surfaces*).—Upper surface: rough, lower surface: moderately smooth.

*Average number of serrations per leaflet*.—20 to 22.

*Leaflet venation type*.—Reticulated.

*Leaflet color* (*both surfaces*).—Upper surface: Green Group NN137 A (Greyish Olive Green). lower surface: Green Group 143 A (Strong Yellow Green).

*Petiole length*.—Medium: 10 to 12 cm.

*Petiole diameter*.—4 to 6 mm.

*Petiole texture*.—Smooth.

*Petiole color*.—Yellow-Green Group N144 D (Strong) Yellow Green).

*Petiolules length*.—6 to 9 mm.

*Petiolules diameter*.—2 to 3 mm.

*Petiolules texture*.—Smooth.

*Petiolules color*.—Yellow-Green Group N144 D (Strong Yellow Green).

*Stipules number*.—2.

*Stipules length*.—11 to 16 mm.

*Stipules width*.—4 to 7 mm.

*Stipules shape*.—Adnate.

*Stipules apex*.—Broadly acuminate to narrowly acute.

*Stipules margin*.—Sinuate.—Undulate.

*Stipules base descriptors*.—Oblique.

*Stipules texture* (*both surfaces*).—Upper surface: moderately smooth. Lower surface: moderately smooth.

*Stipules color of both upper and lower surface*.—Yellow-Green Group 145 B (Light Yellow Green).

Flower description:

*Position of inflorescence in relation to foliage*.—Higher than foliage.

*Inflorescence type*.—Helicoid uniparous cymose.

*Inflorescence length*.—12.5 to 14.0 cm.

*Inflorescence diameter*.—5.5 to 7.0 cm.

*Flower initiation and expression conditions*.—Very low to no cold requirements to flower; early cultivar of day neutral.

*Time of flowering* (50% *of plants at first flower*).—Early, in Uruguay flowers bloom year around, from March through April of the following year.

*Typical number of flowers per truss*.—6 to 9.

*Flower depth*.—2.0 to 2.5 cm.

*Flower diameter*.—3.8 to 5.0 cm.

*Flower lastingness*.—1.5 to 2.5 days.

*Flower fragrance*.—Subtle scent.

*Flower bud shape*.—Pyriform.

*Flower bud length*.—12 to 19 mm.

*Flower bud diameter.*—5 to 30 mm.
*Flower bud texture*.—Smooth.
*Flower bud color*.—Green Group 143 A (Strong Yellow Green).
*Petals*.—Length in relation to width: moderately longer.
*Petal color* (*both surfaces*).—White Group NN155 D (White).
*Petal shape*.—Obovate.
*Petal length.*—12 to 14 mm.
*Petal width.*—12 to 15 mm.
*Petal apex*.—Rounded.
*Petal margin*.—Entire.
*Petal base descriptors*.—Cuneate.
*Petal texture* (*both surfaces*).—Smooth.
*Number of sepals.*—6.
*Sepal shape*.—Acuminate.
*Sepal length.*—11 to 16 mm.
*Sepal width.*—7 to 9 mm.
*Sepal apex.*—Acuminate.
*Sepal margin*.—Ciliate.
*Sepal texture* (*both surfaces*).—Moderately smooth.
*Sepal color of each surface*.—Upper surface: Green Group 137 A (Moderate Olive Green). Lower surface: Green Group 137 D (Moderate Yellowish Green).
*Peduncles & pedicels observed angle.*—35 to 50 degrees.
*Peduncles & pedicels length.*—11.5 to 13.0 cm.
*Peduncles & pedicels diameter.*—4 to 5 mm.
*Peduncles & pedicels texture*.—Smooth.
*Peduncles & pedicels color*.—Yellow-Green Group N144 C (Strong Yellow Green).
*Bracts shape*.—Acuminate.
*Bracts length.*—11 to 13 mm.
*Bracts width.*—4 to 6 mm.
*Bracts texture* (*both surfaces*).—Smooth.
*Bracts color* (*both surfaces*).—Yellow-Green Group 144 A (Strong Yellow Green).

Reproductive organs:
*Observed pistil number.*—300 to 308.
*Observed pistil length.*—0.5 to 1.0 mm.
*Observed pistil color*.—Yellow-Green Group 154 A (Vivid Yellow Green).
*Pollen amount*.—Moderate.
*Stamen number.*—33 to 38.
*Filament length.*—1.5 to 3.0 mm.
*Filament color*.—White Group NN155 D (White).
*Anther shape*.—Sinuous.
*Anther length.*—1.2 to 1.5 mm.
*Anther width.*—0.8 to 1.0 mm.
*Anther color*.—Greyed-Orange Group 163 B (Strong Orange Yellow).

Fruit description:
*Shape*.—Conical
*Season of harvest*.—May thru March.
*Time of ripening* (50% *of plants with first ripe fruit*).—Very early; in Uruguay harvest begins in Mid-May.
*Time of bearing.*—25 to 30 days, depending on weather conditions and season of the year.
*Size*.—Large to very large.
*Fruit length.*—5.2 to 6.0 cm.
*Fruit width.*—4.5 to 5.0 cm.
*Internal fruit color*.—Greyed-Red Group 179 B (Moderate Red).
*Evenness of internal color of fruit flesh*.—Even distribution.
*External fruit color*.—Greyed-Red Group 179 A (Moderate Red).
*Fruit core color*.—Greyed-Red Group 179 C (Moderate Reddish Orange).
*Fruit cavity*.—Present, small and slight. 1 to 1.5 mm×9 to 11 mm.
*Calyx position*.—Inserted.
*Diameter of calyx relative to fruit diameter*.—Much smaller.
*Adherence of calyx*.—Strong.
*Evenness of surface*.—Even or very slightly uneven.
*Glossiness*.—High gloss, great fruit appearance.
*Evenness of color of skin*.—Even distribution.
*Acidity.*—0.5 to 0.65 Titratable acidity (% citric acid).
*Sweetness*.—7.5 to 8.6 brix.
*Firmness*.—Very firm 0.8 to 0.9 N.
*Fruit weight.*—16 g to 25 g.
*Shelf life*.—Six days.
*Achene*.—Level with surface; Width of band without achenes: very narrow.
*Achenes number per berry.*—300 to 308.
*Achenes length.*—0.8 to 1.1 mm.
*Achenes width.*—0.6 to 0.9 mm.
*Achenes weight.*—0.0004 to 0.0005 g.
*Achenes color*.—Yellow-Green Group N144 B (Strong Yellow).
*Everbearing*.—No.

Disease and pest resistance:
*Global response to the disease complex root and stem*.—High field tolerance.
*Resistance to powdery mildew at leaf level*.—Medium-High.
*Resistance to powdery mildew at fruit level*.—Medium-High.
*Resistance to botrytis*.—Low incidence.
*Resistance to spider mites*.—Low preference.
*Resistance to anthracnose in fruit*.—High.

The invention claimed is:

1. A new and distinct variety of strawberry plant named 'LBR 96 1', substantially as illustrated and described herein.

* * * * *